United States Patent

Eberhardt et al.

[11] 4,016,287
[45] Apr. 5, 1977

[54] DERMATOLOGICAL COMPOSITIONS CONTAINING AN ACYLAMINO-CARBOXYLIC ACID OR AN ALKYL ESTER THEREOF

[75] Inventors: Hans Eberhardt; Rolf Stefan Brickl, both of Biberach an der Riss, Germany

[73] Assignee: Boehringer Ingelheim GmbH, Ingelheim am Rhein, Germany

[22] Filed: July 17, 1975

[21] Appl. No.: 596,852

Related U.S. Application Data

[63] Continuation-in-part of Ser. No. 379,751, July 16, 1973, abandoned.

[52] U.S. Cl. .................. 424/309; 424/311; 424/319
[51] Int. Cl.[2] .......................... A61K 31/24
[58] Field of Search .............. 424/309, 311, 319
[56] References Cited

UNITED STATES PATENTS

| | | | |
|---|---|---|---|
| 2,689,170 | 9/1954 | King | 424/54 |
| 3,235,457 | 2/1966 | Laden | 424/65 |

OTHER PUBLICATIONS

Lobowe O-T-C Antiseborrheic Preparations Handbook of Non-Prescription Drugs, pp. 86–89 (1967).
Jungermann et al. J.A.C.S. 78 172–174 (1956).
Chemical Abstracts 74:60692q (1971).
Chemical Abstracts 66:29058g (1967).

*Primary Examiner*—Leonard Schenkman
*Attorney, Agent, or Firm*—Hammond & Littell

[57] ABSTRACT

Topical dermatological compositions containing an acylamino-carboxylic acid compound of the formula

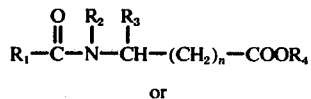

or

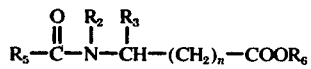

wherein
$R_1$ is hydrogen, alkyl of 1 to 3 carbon atoms, trifluoromethyl, phenyl, halo-phenyl, nitro-phenyl or biphenylyl,
$R_2$ is hydrogen or alkyl of 1 to 3 carbon atoms,
$R_3$ is hydrogen, alkyl of 1 to 6 carbon atoms, methylthio-(alkyl of 1 to 6 carbon atoms) or benzyl,
$R_4$ is alkyl of 10 to 22 carbon atoms,
$n$ is 0, 1 or 2,
$R_5$ is alkyl of 8 to 22 carbon atoms, phenyl or biphenylyl, and
$R_6$ is hydrogen or alkyl of 1 to 3 carbon atoms; the compositions are useful for the care of the skin.

6 Claims, No Drawings

DERMATOLOGICAL COMPOSITIONS CONTAINING AN ACYLAMINO-CARBOXYLIC ACID OR AN ALKYL ESTER THEREOF

This is a continuation-in-part of copending application Ser. No. 379,751 filed July 16, 1973, now abandoned.

This invention relates to novel topical dermatological compositions containing an acylamino-carboxylic acid or an alkyl ester thereof, and a method of caring for the skin therewith.

Numerous acylamino-carboxylic acids and derivatives thereof have been described in the literature [see, for example, C.A. 66, 29058 (1967)], but no biological activity whatever has been ascribed to such compounds.

We have discovered that compounds of the formula

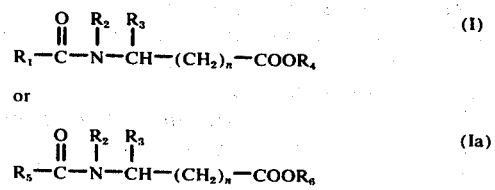

wherein
$R_1$ is hydrogen, alkyl of 1 to 3 carbon atoms, trifluoromethyl, phenyl, halo-phenyl, nitro-phenyl or biphenylyl,
$R_2$ is hydrogen or alkyl of 1 to 3 carbon atoms,
$R_3$ is hydrogen, alkyl of 1 to 6 carbon atoms, methylthio-(alkyl of 1 to 6 carbon atoms) or benzyl,
$R_4$ is alkyl of 10 to 22 carbon atoms,
$n$ is 0, 1 or 2,
$R_5$ is alkyl of 8 to 22 carbon atoms, phenyl or biphenylyl, and
$R_6$ is hydrogen or alkyl of 1 to 3 carbon atoms;
have certain therapeutic and cosmetic properties which render them useful as active ingredients in topical dermatological compositions.

The compounds embraced by formulas I and Ia, most of which are described in the literature, may be prepared by acylating a compound of the formula

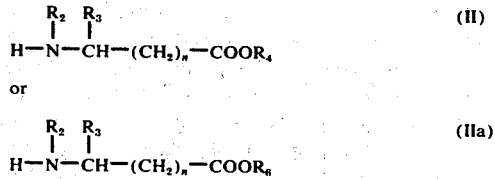

wherein $R_2$, $R_3$, $R_4$, $R_6$ and $n$ have the same meanings as in formulas I and Ia, or an acid addition salt thereof, with, respectively, a reactive derivative of a carboxylic acid of the formula $$R_1 - COOH \quad (III)$$

or $$R_5 - COOH \quad (IIIa)$$

wherein $R_1$ and $R_5$ have the same meanings as in formulas I and Ia.

The acylation is preferably performed in a solvent medium, such as water, and in the presence of a base, such as sodium hydroxide or pyridine, at a temperature between 0° and 100° C. The preferred embodiments of reactive derivatives of an acid of the formulas III and IIIa are anhydrides and halides.

The following examples illustrate the preparation of various compounds of the formulas I and Ia:

EXAMPLE A

Octadecyl ester of N-acetyl-glycine

A mixture consisting of 3.0 gm of glycine ethyl ester hydrochloride and 15.0 gm of octadecanol was heated to 100° C and, while maintaining the molten mixture at that temperature, gaseous hydrogen chloride was introduced therein over a period of 3 hours. Thereafter, the reaction mixture was allowed to cool, the solidified mass was suspended in 500 ml of ether, and the solid, insoluble residue, glycine octadecyl ester hydrochloride, was collected by vacuum filtration. The filter cake was suspended in water and, while stirring the aqueous suspension, an excess of sodium bicarbonate was added thereto, whereby the free base, glycine octadecyl ester, was liberated. The ester was collected by vacuum filtration, dried, added to 50 ml of acetic acid anhydride, and the mixture was heated for one hour on a boiling water bath. Thereafter, the resulting reaction solution was added to 1 liter of water, and the precipitate formed thereby was collected by vacuum filtration and dried. The raw product was purified by recrystallizing three times from petroleum ether, yielding 2.1 gm (26% of theory) of the compound of the formula

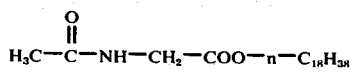

with a melting point of 78°–79° C. This compound is not described in the prior art.

EXAMPLE B

N-Octadecanoyl-glycine (a known compound)

7.5 gm (0.1 mol) of glycine were dissolved in a solution of 4.0 gm (0.1 mol) of sodium hydroxide in 150 ml of water, 30 gm (0.1 mol) of octadecanoyl chloride were added to the resulting solution, and the mixture was vigorously shaken until the reaction product became solid. The reaction mixture was then acidified with concentrated hydrochloric acid, vacuum-filtered, and the filter cake was washed with water, dried and recrystallized twice from ethyl acetate, yielding 25 gm (73% of theory) of the compound of the formula

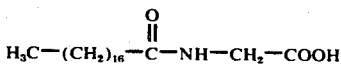

which had a melting point of 120° C.

In like manner, using a procedure analogous to that in Example A or B, respectively, the following additional acylamino-carboxylates and -carboxylic acids were prepared [see also Rec. trav. chim. 77, 267 (1958); and J.A.C.S. 78, 172 (1956)]:

N-acetyl-leucine hexadecyl ester, m.p. 37°–38° C
N-acetyl-methionine hexadecyl ester, m.p. 59°–60° C
N-acetyl-phenylalanine hexadecyl ester, m.p. 75°–76° C
N-acetyl-sarcosine hexadecyl ester, m.p. 58°–59° C
N-formyl-glycine hexadecyl ester, m.p. 64°–65° C
N-propionyl-glycine hexadecyl ester, m.p. 67°–68° C N-trifluoroacetyl-glycine hexadecyl ester, m.p. 68°–70° C
N-benzoyl-glycine hexadecyl ester, m.p. 59°–60° C
N-(4-phenyl-benzoyl)-glycine hexadecyl ester, m.p. 103° C
N-(4-chloro-benzoyl)-glycine hexadecyl ester, m.p. 85°–86° C
N-(4-nitro-benzoyl)-glycine hexadecyl ester, m.p. 102°–103° C
N-acetyl-β-alanine hexadecyl ester, m.p. 65°–66° C
N-benzoyl-glycine docosyl ester, m.p. 78°–79° C
N-acetyl-glycine dodecyl ester, m.p. 59°–60° C
N-acetyl-glycine tridecyl ester, m.p. 65°–66° C
N-acetyl-glycine tetradecyl ester, m.p. 69°–70° C
N-acetyl-glycine pentadecyl ester, m.p. 73°–74° C
N-acetyl-glycine hexadecyl ester, m.p. 74°–75° C
N-acetyl-glycine heptadecyl ester, m.p. 76°–77° C
N-acetyl-glycine octadecyl ester, m.p. 78°–79° C
N-acetyl-glycine nonadecyl ester, m.p. 79°–80° C
N-acetyl-glycine eicosyl ester, m.p. 83°–84° C
N-acetyl-glycine docosyl ester, m.p. 86°–87° C
N-acetyl-alanine hexadecyl ester, m.p. 64°–65° C
N-acetyl-alanine octadecyl ester, m.p. 70°–71° C
N-acetyl-β-alanine eicosyl ester, m.p. 76° C
N-acetyl-β-alanine dodecyl ester, m.p. 50° C
N-benzoyl-β-alanine dodecyl ester, m.p. 56° C
N-acetyl-4-amino-butyric acid tetradecyl ester, m.p. 58° C
N-acetyl-4-amino-butyric acid octadecyl ester, m.p. 71° C
N-benzoyl-4-amino-butyric acid octdecyl ester, m.p. 76° C
N-dodecanoyl-glycine*, m.p. 120° C
N-tetradecanoyl-glycine*, m.p. 125° C
N-hexadecanoyl-glycine*, m.p. 123°–126° C
N-docosanoyl-glycine*, m.p. 121° C
N-octadecanoyl-alanine*, m.p. 109° C
N-dodecanoyl-valine, m.p. 107° C
N-tetradecanoyl-valine*, m.p. 98° C
N-octadecanoyl-valine*, m.p. 93° C
N-dodecanoyl-leucine*, m.p. 109° C
N-tetradecanoyl-leucine*, m.p. 102° C
N-hexadecanoyl-leucine*, m.p. 88°–89° C
N-octadecanoyl-leucine*, m.p. 96° C
N-docosanoyl-leucine*, m.p. 98° C
N-hexadecanoyl-sarcosine*, m.p. 65°–66° C
N-octanoyl-glycine*, m.p. 109° C
N-decanoyl-glycine*, m.p. 114° C
N-hexadecanoyl-β-alanine, m.p. 117°–118° C
N-benzoyl-β-alanine, m.p. 103°–105° C
N-5-phenylbenzoyl-β-alanine, m.p. 103°–105° C
N-dodecanoyl-4-amino-butyric acid*, m.p. 92°–93° C
N-octadecanoyl-4-amino-butyric acid, m.p. 100°–102° C
N-benzoyl-4-amino-butyric acid, m.p. 88°–89° C
N-4'-phenylbenzoyl-4-amino-butyric acid, m.p. 181° C
N-tetradecanoyl-sarcosine*, m.p. 51°–52° C
N-octadecanoyl-sarcosine*, m.p. 71°–72° C
N-dodecanoyl-alanine*, m.p. 104°–105° C
N-dodecanoyl-phenylalanine*, m.p. 100° C
N-hexadecanoyl-phenylalanine*, m.p. 98°–99° C
N-octadecanoyl-glycine methyl ester*, m.p. 83°–84° C
N-octadecanoyl-glycine ethyl ester*, m.p. 82°–83° C
N-octadecanoyl-alanine methyl ester*, m.p. 76°–77° C
N-octadecanoyl-phenylalanine iopropyl ester*, m.p. 69°–70° C.

In the above list of compounds, those followed by an asterisk (*) are compounds which are described in the prior art, while those not followed by an asterisk are not specifically disclosed in the prior art.

As indicated above, we have ascertained that the compounds embraced by formulas I and Ia have certain useful cosmetic and therapeutic properties, and that when they are incorporated into conventional topical dermatological formulations, such as ointments, creams, aerosol sprays, powders, tinctures, gels, pastes, bath oils, lotions or the like, in concentrations of 0.1 to 20% by weight, preferably 0.25 to 5% by weight, based on the total weight of the composition, such compositions are effective for the care and treatment of the skin. More particularly, such compositions exhibit sebaceous gland excretion-inhibiting, antiphlogistic, anti-proliferative, dandruff-inhibiting, capillary-stablizing, local anesthetic and moisturizing activities.

Particularly effective are those compounds of the formula I wherein $R_1$ is methyl, ethyl, phenyl or biphenylyl, $R_2$ and $R_3$ are hydrogen, $R_4$ is hydrogen or alkyl of 14 to 18 carbon atoms, and $n$ is 0, 1 or 2.

The sebaceous gland excretion-inhibiting and antiphlogistic activities of the compounds of the formulas I and Ia were ascertained by the methods described below, and the results obtained are shown for a few representative species, where A = N-acetyl-glycine hexadecyl ester
B = N-acetyl-alanine hexadecyl ester
C = N-benzoyl-glycine hexadecyl ester
D 32 N-acetyl-sarcosine hexadecyl ester
E = N-octadecanoyl
F = N-formyl-glycine hexadecyl ester
G = N-propionyl-glycine hexadecyl ester
H = N-tetradecanoyl-glycine
I = N-(4'-phenyl-benzoyl)-4-amino-butyric acid
J = N-acetyl-β-alanine hexadecyl ester The sebaceous gland excretion-inhibiting activity was ascertained by the glass block method described by Schaefer and Kuhn-Bussius in Arch. Klin. exper. Derm. 238, 429–435 (1970). Small glass blocks, the facets of which have been roughened or frosted, are pressed against the skin surface where the amount of skin fat is measured. The skin fat or sebum transferred from the skin to the glass facet makes the blocks more translucent, and the increase in translucence is directly proportional to the amount of sebum present in the skin area. The translucence is measured in a photometer. Prior to measurement of the degree of refating of the skin, the skin fat was removed with a plastic foil.

0.25 ml of an ethanolic 5% solution of the compound to be tested was applied to half of the forehead of 5 to 10 human test subjects, while 0.25 ml of ethanol was applied to half of the forehead of a group of 5 to 10 control subjects. After 90 minutes the skin fat was removed with the plastic foil, and after three additional hours the degree of refatting was determining with the aid of the small glass blocks referred to above. The following results were obtained:

| Compound | Average extinction values | | |
|---|---|---|---|
| | Controls | Treated | Difference |
| A | 66.0 | 75.5 | 9.5 |
| B | 66.5 | 74.0 | 7.5 |
| C | 62.0 | 78.5 | 16.5 |
| D | 77.5 | 86.5 | 9.0 |
| E | 60.0 | 78.0 | 18.0 |

The antiphlogistic activity was ascertained by the dinitrochlorobenzene-eczema method [see A. I. Scott, Brit. J. Dermatol. 77, 586 (1965)].

The compound to be tested was applied in the form of an ethanolic 5% solution to the shaved flanks of a group of 10 guinea pigs which has been sensitized with dinitrochlorobenzene. An analogous control group was treated with only ethanol. The treatment was effected 30 minutes prior to release of the allergic reaction with a 1% solution of dinitrochlorobenzene in acetone. The results were visually evaluated 22 hours thereafter. The following results were obtained:

| Compound | Inhibition of dinitrochlorobenzene-eczema over control in % |
|---|---|
| F | 50 |
| A | 46 |
| G | 34 |
| C | 28 |
| K | 30 |
| D | 20 |
| B | 19 |
| H | 38 |
| I | 36 |
| J | 35 |

The compounds embraced by formulas I and Ia are, for practical purposes, completely non-toxic; for instance, the $LD_{50}$ of compound C is greater than 4000 mgm/kg mouse i.p.

In addition to one or more compounds of the formula I or Ia, a composition of the present invention may also contain one or more other active ingredients, such as vitamins, corticosteroids, steroids, antihistamines, keratolytics, antibiotics or disinfectants.

The following examples illustrate a few topical compositions for the cosmetic and/or therapeutic treatment of the skin, which comprise a compound of the formula I or Ia. The parts are parts by weight unless otherwise specified.

EXAMPLE 1

Cream

The cream composition is compounded from the following ingredients:

| | |
|---|---|
| N-Acetyl-glycine hexadecyl ester | 3.0 parts |
| Benzalkonium chloride | 0.1 parts |
| Cremophor O[1] | 4.0 parts |
| Glycerine monostearate | 4.0 parts |
| Lanette O[2] | 5.0 parts |
| Spermaceti | 3.0 parts |
| Cetiol V[3] | 10.0 parts |
| Distilled water   q.s.ad | 100.0 parts |

[1]Long-chain, high-molecular, water soluble, wax-like polyglycolether; a commercial cosmetic and pharmaceutical emulsifier for high-molecular alcohols, fatty acids, waxes, wool grease, spermaceti, etc.
[2]Mixture of cetyl and stearyl alcohols; a commercial neutral, skin-compatible, consistancy-imparting factor for ointments, creams and emulsions.
[3]Mixture of esters of unsaturated fatty acids, mainly oleyl oleate; a commercial, conventional, skin-penetrating, low-viscosity liquid additive for cosmetic creams and the like.

Preparation:

The benzalkonium chloride is dissolved in the distilled water at 70° C (I). The glycine ester is homogeneously suspended in the molten (70° C) mixture of the Cremophor, the glycerin monostearate, the Lanette, the spermaceti and the Cetiol (II). Suspension II is emulsified at 70° C into solution I, and the composition is stirred until cool.

EXAMPLE 2

Ointment

The ointment is compounded from the following ingredients:

| | |
|---|---|
| N-Benzoyl-glycine hexadecyl ester | 3.0 parts |
| Cremophor O | 6.0 parts |
| Cremophor A solid[4] | 1.0 parts |
| Wool grease | 2.0 parts |
| Paraffin oil | 45.0 parts |
| Vaseline     q.s.a.d. | 100.0 parts |

Preparation:

The Cremophors, the wool grease, the paraffin oil and the vaseline are admixed with each other, the mixture is melted by heating to 70° C, the glycine ester is suspended in the molten mixture, and the composition is stirred until cool.

EXAMPLE 3

Gel

The gel is compounded from the following ingredients:

| | |
|---|---|
| N-Acetyl-glycine hexadecyl ester | 3.0 parts |
| Carbopol 940[5] | 0.6 parts |
| Triethanolamine | 0.6 parts |
| Cremophor EL[6] | 5.0 parts |
| Isopropanol | 30.0 parts |
| Distilled water     q.s.a.d. | 100.0 parts |

[5]Carboxypolymethylene; carboxyvinyl polymer with very high molecular weight; form colloidal solutions with water; a commercial thickening agent for cosmetics.
[6]A viscous oil similar in composition to Cremophor O and A; a commercial emulsifier for cosmetics.

Preparation:

The glycine ester, the Cremophor and the triethanolamine are dissolved in the isopropanol, and the resulting solution is stirred into the solution of the Carbopol in the distilled water.

EXAMPLE 4

Bath oil

The composition is compounded from the following ingredients:

| | |
|---|---|
| N-Acetyl-glycine hexadecyl ester | 5.0 parts |
| Texapon N 25[7] | 30.0 parts |
| Comperlan OD[8] | 5.0 parts |
| Isopropanol | 20.0 parts |
| Ethereal oil | 2.0 parts |
| Distilled water     q.s.a.d. | 100.0 parts |

[7]Fatty alcohol ether sulfate; a commercial washing, wetting and dispersing agent.
[8]A fatty acid alkylolamide; commercial consistency-imparting factor for cosmetic and pharmaceutical preparations.

Preparation:

The glycine ester and the ethereal oil are dissolved in the isopropanol, and the resulting solution is stirred into the solution of the Texapon and the Comperlan in the distilled water.

EXAMPLE 5

Hair tonic

The composition is compounded from the following ingredients:

| | |
|---|---|
| N-Tetradecanoyl-glycine | 0.25 parts |
| Diisopropyl adipate | 0.2 parts |
| Perfume oil | 0.1 parts |
| Isopropanol | 50.0 parts |
| Distilled water    q.s.a.d. | 100.0 parts |

Preparation:

The glycine derivative, the adipate and the perfume oil are dissolved in the isopropanol, and the resulting solution is admixed with the distilled water by stirring.

EXAMPLE 6

Aerosol dry spray

The spray is compounded from the following ingredients:

| | |
|---|---|
| N-Acetyl-glycine hexadecyl ester | 3.0 parts |
| Span 85 | 0.4 parts |
| Frigen 11 A | 3.0 parts |
| Frigen 12/114 (40:60) | 93.6 parts |

Preparation:

The glycine ester, the Span and the Frigen 11 are intimately admixed in a ball mill, the mixture is cooled to −15° C and slowly introduced into the Frigen 12/114 mixture at −40° to −50° C, and the composition is filled into aerosol containers, accompanied by stirring.

EXAMPLE 7

Aerosol foam

The foam composition is compounded from the following ingredients:

| | |
|---|---|
| N-Benzoyl-glycine hexadecyl ester | 3.0 parts |
| Cremophor EL | 1.0 parts |
| Tween 80 | 1.2 parts |
| Texapon N 25 | 0.8 parts |
| Ethanol (94%) | 21.0 parts |
| Distilled water | 57.0 parts |
| Frigen 12/114 (60:40) | 16.0 parts |

Preparation:

The glycine ester is dissolved in the ethanol (solution I). The Cremophor, the Tween and the Texapon are dissolved in the distilled water (solution II). Solution I is stirred into solution II, and the resulting concentrate is filled into aerosol cans. After the valve has been affixed to the filled cans, the propellant gas mixture is introduced under pressure.

EXAMPLE 8

Cream

The composition is compounded from the following ingredients:

| | |
|---|---|
| N-Benzoyl-glycine hexadecyl ester | 3.0 parts |
| Benzalkon A | 0.1 parts |
| Cremophor O | 4.0 parts |
| Glycerine monostearate | 4.0 parts |
| Lanette O | 5.0 parts |
| Spermaceti | 3.0 parts |
| Cetiol V | 10.0 parts |
| Vitamin A acetate | 30,000 I.U. |
| Vitamin E acetate | 20 I.U. |

-continued

| | |
|---|---|
| Distilled water    q.s.a.d. | 100.0 parts |

The composition is compounded in a manner analogous to that described in Example 1.

EXAMPLE 9

Lotion

The lotion is compounded from the following ingredients:

| | |
|---|---|
| N-Octadecanoyl-glycine | 3.0 parts |
| Span 40 | 1.0 parts |
| Cremophor O | 2.0 parts |
| Lanette O | 2.0 parts |
| Spermaceti | 1.0 parts |
| Cetiol V | 5.0 parts |
| Paraffin oil, soluble | 1.0 parts |
| Methylparaben | 0.1 parts |
| Distilled water    q.s.a.d. | 100.0 parts |

Preparation:

The Span, the Cremophor, the Lanette, the spermaceti, the Cetiol and the paraffin oil are admixed with each other, the mixture is melted at 70° C, and the glycine derivative is dissolved in the molten mixture. The distilled water is heated to 80° C, the methylparaben is dissolved therein, the resulting solution is cooled to 70° C and added to the molten fatty mixture, and the composition is homogenized and stirred until cool.

EXAMPLE 10

Shampoo

The shampoo is compounded from the following ingredients:

| | |
|---|---|
| N-Acetyl-glycine hexadecyl ester | 3.0 parts |
| Zetesol SE 35T | 55.0 parts |
| Methyl cellulose | 1.0 parts |
| Perfume oil | 0.2 parts |
| Methylparaben | 0.5 parts |
| Distilled water    q.s.a.d. | 100.0 parts |

Preparation:

The distilled water is heated to 80° C, the methylparaben is dissolved therein, and the methyl cellulose is suspended in the aqueous solution. The Zetesol and the perfume oil are admixed with each other, the glycine ester is dispersed in the mixture with a high-speed stirrer, the dispersion is added to the methyl cellulose slurry, and the resulting composition is homogenized and purged of air.

EXAMPLE 11

Powder

The powder is compounded from the following ingredients:

| | |
|---|---|
| N-Acetyl-glycine hexadecyl ester | 3.0 parts |
| Colloidal silicic acid | 1.0 parts |
| Magnesium stearate | 0.2 parts |
| ANM corn starch    q.s.a.d. | 100.0 parts |

Preparation:

The glycine ester, the colloidal silicic acid and the magnesium stearate are successively added to about one-third of the indicated amount of the corn starch, the mixture is thoroughly blended, the remaining amount of corn starch is added thereto, and the resulting composition is again thoroughly blended.

EXAMPLE 12

Paste

The paste is compounded from the following ingredients:

| | |
|---|---|
| N-(4'-Phenyl-benzoyl)-4-amino-butyric acid | 3.0 parts |
| Lanogen 1500[9] | 20.0 parts |
| Isopropanol | 45.0 parts |
| Veegum[10] pharm. | 10.0 parts |
| Pigment + dye | 1.0 parts |
| Perfume oil | 0.2 parts |
| Distilled water q.s.a.d. | 100.0 parts |

[9]A commercial ointment base made from polyethyleneglycol.
[10]Flocculated colloidal magnesium aluminum silicate; a commercial emulsifying, suspending and thickening agent.

Preparation:

The butyric acid derivative is dissolved in the ointment base at 60° C (solution I). The perfume oil is dissolved in the isopropanol (solution II). The distilled water is heated to 60° C, the Veegum is dispersed therein and allowed to swell, solutions I and II and the pigment and dye are added thereto, and the composition is thoroughly kneaded and homogenized.

EXAMPLE 13

Tincture

The tincture is compounded from the following ingredients:

| | |
|---|---|
| N-Benzoyl-glycine hexadecyl ester | 3.0 parts |
| Isopropanol | 25.0 parts |
| Ethanol (96%), pure | 25.0 parts |
| Perfume oil | 0.2 parts |
| Distilled water q.s.a.d. | 100.0 parts |

Preparation:

The isopropanol is admixed with the ethanol, the mixture is heated to 60° C, the glycine ester and the perfume oil are dissolved therein, the distilled water is added to the solution, and the resulting aqueous mixture is cooled to room temperature and filtered.

EXAMPLE 14

Gel with antibiotic

The gel is compounded from the following ingredients:

| | |
|---|---|
| N-Acetyl-glycine hexadecyl ester | 3.0 parts |
| Chloramphenicol or tetracycline . HCl | 0.1 parts |
| Salicylic acid | 0.5 parts |
| Isopropanol | 25.0 parts |
| Bentone EW[11] | 2.0 parts |
| Triethanolamine | 1.8 parts |
| Distilled water q.s.a.d. | 100.0 parts |

[11]Organic derivatives of hydrous magnesium aluminum silicate materials; a commercial gelling agent for viscosity and flow control.

Preparation:

The Bentone is stirred with a high-speed stirrer into about two-thirds of the required amount of distilled water and allowed to swell therein (I). The salicylic acid and the triethanolamine are dissolved in the remainder of the water (II). The glycine ester and the antibiotic is dissolved in the isopropanol (III). II and III are added to I while stirring, and the resulting composition is homogenized and purged of air.

While the above composition examples illustrate only a few specific compounds of the formulas I and Ia as an active ingredient, it should be understood that any of the other compounds embraced by formulas I and Ia may be substituted therefor in Examples 1 through 14.

Likewise, the amount of active ingredient in these illustrative examples may be varied to achieve the concentration range set forth above, and the amounts and nature of the inert carried ingredients may be varied to meet particular requirements.

While the present invention has been illustrated with the aid of certain specific embodiments therefore, it will be readily apparent to others skilled in the art that the invention is not limited to these particular embodiments, and that various changes and modifications may be made without departing from the spirit of the invention or the scope of the appended claims.

We claim:

1. A method of inhibiting the sebaceous gland exectretion and combatting inflammations of the skin, which comprises topically applying to the skin an effective amount of a composition consisting essentially of an inert dermatological carrier and from 0.1 to 20% by weight, based on the total weight, of a compound of the formula

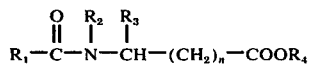

wherein
$R_1$ is hydrogen, alkyl of 1 to 3 carbon atoms, trifluoromethyl, phenyl, halo-phenyl, nitro-phenyl or biphenylyl,
$R_2$ is hydrogen, alkyl of 1 to 3 carbon atoms or phenyl,
$R_3$ is hydrogen, alkyl of 1 to 6 carbon atoms, methylthio-ethyl or benzyl,
$R_4$ is alkyl of 10 to 22 carbon atoms or, when $R_1$ is biphenylyl, also hydrogen, and
$n$ is 0, 1 or 2.

2. The method of claim 1 wherein said compound is of the formula

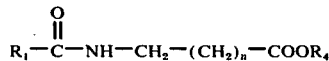

wherein
$R_1$ is methyl, ethyl, phenyl, chloro-phenyl or biphenylyl,
$R_4$ is alkyl of 14 to 18 carbon atoms, and
$n$ is 0, 1 or 2.

3. The method of claim 1,
where
$R_1$ is hydrogen, alkyl of 1 to 3 carbon atoms, trifluoromethyl, phenyl, halo-phenyl, nitro-phenyl or biphenylyl,
$R_2$ is hydrogen or alkyl of 1 to 3 carbon atoms, R₃ is hydrogen, alkyl of 1 to 6 carbon atoms, methylthio-ethyl or benzyl, R₄ is alkyl of 10 to 22 carbon atoms, n is 0, 1 or 2.

4. The method of claim 1, where said compound is N-acetyl-glycine hexadecyl ester.

5. The method of claim 1, where said compound is N-benzoyl-glycine hexadecyl ester.

6. The method of claim 1, where said compound is N-(4'-phenyl-benzoyl)-4-amino-butyric acid.

* * * * *

UNITED STATES PATENT OFFICE
CERTIFICATE OF CORRECTION

Patent No. 4,016,287                    Dated April 5, 1977

Inventor(s) Hans Eberhardt et al.

It is certified that error appears in the above-identified patent and that said Letters Patent are hereby corrected as shown below:

Column 3, line 51 - "N-5-" should read -- N-4- --

" 4, " 29 - "32" should read -- = --

" " " 31 - After "octadecanoyl", insert ---glycine --

" 6, " 14 - After the table, insert -- $^4$Non-ionic derivative of fatty substance with polyethylene-oxide radical; a commercial water-dispersible emulsifier for paraffin oil, vaseline and vegetable oils. --

Signed and Sealed this

Seventh Day of June 1977

[SEAL]

Attest:

RUTH C. MASON
Attesting Officer

C. MARSHALL DANN
Commissioner of Patents and Trademarks